US008238515B2

(12) United States Patent
Birnbaum et al.

(10) Patent No.: US 8,238,515 B2
(45) Date of Patent: Aug. 7, 2012

(54) WELL PLATE

(75) Inventors: Eva R. Birnbaum, Los Alamos, NM (US); Benjamin P. Warner, Los Alamos, NM (US); Sharon M. Baldwin, Sante Fe, NM (US); Jennifer A. Berger, Los Alamos, NM (US); Rebecca L. E. Miller, Los Alamos, NM (US)

(73) Assignee: Caldera Pharmaceuticals, Inc., Los Alamos, NM (US)

( * ) Notice: Subject to any disclaimer, the term of this patent is extended or adjusted under 35 U.S.C. 154(b) by 279 days.

(21) Appl. No.: 12/192,762

(22) Filed: Aug. 15, 2008

(65) Prior Publication Data

US 2009/0046832 A1    Feb. 19, 2009

Related U.S. Application Data

(60) Provisional application No. 60/965,052, filed on Aug. 16, 2007.

(51) Int. Cl.
 *G01N 23/223* (2006.01)
(52) U.S. Cl. ........................................... 378/44; 378/47
(58) Field of Classification Search .............. 378/44–50, 378/79
 See application file for complete search history.

(56) References Cited

U.S. PATENT DOCUMENTS

| | | | |
|---|---|---|---|
| 6,326,144 B1 * | 12/2001 | Bawendi et al. | 435/6 |
| 6,878,553 B1 * | 4/2005 | Li et al. | 436/174 |
| 7,342,995 B2 * | 3/2008 | Sato et al. | 378/46 |
| 2003/0053589 A1 | 3/2003 | Ikeshita et al. | |
| 2005/0054626 A1 * | 3/2005 | Carter et al. | 514/210.01 |
| 2005/0225756 A1 * | 10/2005 | Khamizov et al. | 356/246 |
| 2005/0245485 A1 * | 11/2005 | Lanter et al. | 514/63 |
| 2006/0029955 A1 * | 2/2006 | Guia et al. | 435/6 |
| 2006/0078902 A1 | 4/2006 | Bunting et al. | |
| 2007/0207509 A1 * | 9/2007 | Frederickson et al. | 435/7.23 |

OTHER PUBLICATIONS

G.A. Chandler et al, "Filtered x-ray diode diagnostics fielded on the Z accelerator for source power measurements." Review of Scientific Instruments. vol. 70, No. 1, Jan. 1999. pp. 561-565. Published by: American Institue of Physics. Copyright: 1999.

* cited by examiner

*Primary Examiner* — Hoon Song

(57) ABSTRACT

The present invention includes an apparatus for preparing samples for measurement by x-ray fluorescence spectrometry. The apparatus comprises a plate having one or more holes passing through the plate. The holes are covered by a film on one side of the plate. The holes are less than 500 micrometers across in one dimension where the film covers the holes. The film is translucent to x-rays. The present invention also includes an apparatus for preparing samples for measurement by x-ray fluorescence spectrometry. The apparatus comprises a plate having one or more holes passing through the plate. The holes are covered on one side of the plate by a detachable cover forming a water-tight seal against the plate. The cover is substantially free of the elements osmium, yttrium, iridium, phosphorus, zirconium, platinum, gold, niobium, mercury, thallium, molybdenum, sulfur, lead, bismuth, technetium, ruthenium, chlorine, rhodium, palladium, argon, silver, and thorium. The holes are less than about 500 micrometers across in one dimension where the cover covers the holes. The present invention also includes a method for preparing samples for measurement by x-ray fluorescence spectrometry. The method comprises providing a solution of with less than 10 micromolar solute and a volume of between about 2 microliters and about 2 milliliters. The solution is concentrated and analyzed using x-ray fluorescence spectrometry.

15 Claims, 5 Drawing Sheets

Protein Sample Deposited Using Apparatus 2

Protein Spot Deposited by Pipette

WELL PLATE

RELATED APPLICATIONS

This application is related to and claims the priority of U.S. Provisional Patent Application 60/965,052 entitled "Well Plate," which was filed on Aug. 16, 2007, which is incorporated by reference herein.

FIELD OF THE INVENTION

The present invention relates to the preparation of samples for spectroscopic analysis.

BACKGROUND OF THE INVENTION

X-ray fluorescence (XRF) spectrometry is a powerful spectroscopic technique that has been used to determine the elements that are present in a chemical sample, and to determine the quantity of those elements in the sample. The underlying physical principle of the method is that when an atom of a particular element is irradiated with X-ray radiation, the atom ejects a core electron such as a K shell electron. The resulting atom is then in an excited state, and it can return to the ground state by replacing the ejected electron with an electron from a higher energy orbital. This is accompanied by the emission of a photon. The energy of the emitted photons is equal to the difference in the energies of the two orbitals. Each element has a characteristic set of orbital energies and therefore, a characteristic X-ray fluorescence (XRF) spectrum.

An XRF spectrometer is an apparatus capable of irradiating a sample with an X-ray beam, detecting the X-ray fluorescence from the sample, and using the X-ray fluorescence to determine which elements are present in the sample and measuring the quantity of these elements. A typical, commercially available energy dispersive X-ray fluorescence spectrometer is the EDAX Eagle XPL energy dispersive X-ray fluorescence spectrometer, equipped with a microfocus X-ray tube, lithium drifted silicon solid-state detector, processing electronics, and vendor supplied operating software, available from the EDAX division of Ametek, 91 McKee Drive Mahwah, N.J. 07430. An example of a wavelength dispersive X-ray fluorescence spectrometer is the ZSX Primus, available from Rigaku Americas, 9009 New Trails Drive, The Woodlands, Tex. 77381. In principle, any element may be detected and quantified with XRF.

Typical protein-drug assays are performed with anomala to micromolar protein concentrations and drug concentrations. The protein concentration and the drug concentration need not be the same. The existing art for the analysis of dried samples by x-ray fluorescence can only measure dried samples which are deposited from one micro liter or less of solutions having minimum concentrations of about 10 micromolar (see Thomason C. Miller, Christopher M. Sparks, George J. Avilla, Meredith R. Beebe, Semiconductor applications of manlier droplet methodology with total reflection X-ray fluorescence analysis, Spectrochimica Acta Part B 59 (2004) 1117-1124, incorporated herein by reference). This sample preparation method is insufficient for the analysis of proteins and protein-drug complexes, where biologically relevant concentrations of the solution from which the sample is deposited must be less than 10 micromolar and preferably less than 100 nanomolar.

The existing state of the art is insufficient for analyzing dilute solutions, especially dilute solutions of proteins having concentrations of less than about 10 micromolar.

There remains a need for simpler methods for preparing samples for measurement using x-ray fluorescence spectrometry. The present invention is designed to address that need.

SUMMARY OF THE PRESENT INVENTION

One aspect of the present invention includes an apparatus for preparing samples for measurement by x-ray fluorescence spectrometry. The apparatus comprises a plate having one or more holes passing through the plate. The holes are covered by a film on one side of the plate. The holes are less than 500 micrometers across in one dimension where the film covers the holes. The film is translucent to x-rays.

Another aspect of the present invention comprises an apparatus for preparing samples for measurement by x-ray fluorescence spectrometry. The apparatus comprises a plate having one or more holes passing through the plate. The holes are covered on one side of the plate by a detachable cover forming a water-tight seal against the plate. The cover is substantially free of the elements osmium, yttrium, iridium, phosphorus, zirconium, platinum, gold, niobium, mercury, thallium, molybdenum, sulfur, lead, bismuth, technetium, ruthenium, chlorine, rhodium, palladium, argon, silver, and thorium. The holes are less than about 500 micrometers across in one dimension where the cover covers the holes.

Still another aspect of the present invention includes a method for preparing samples for measurement by x-ray fluorescence spectrometry. The method comprises providing a solution with less than 10 micromolar solute and a volume of between about 2 microliters and about 2 milliliters. The solution is concentrated and analyzed using x-ray fluorescence spectrometry.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DETAILED DESCRIPTION

Figure 1:
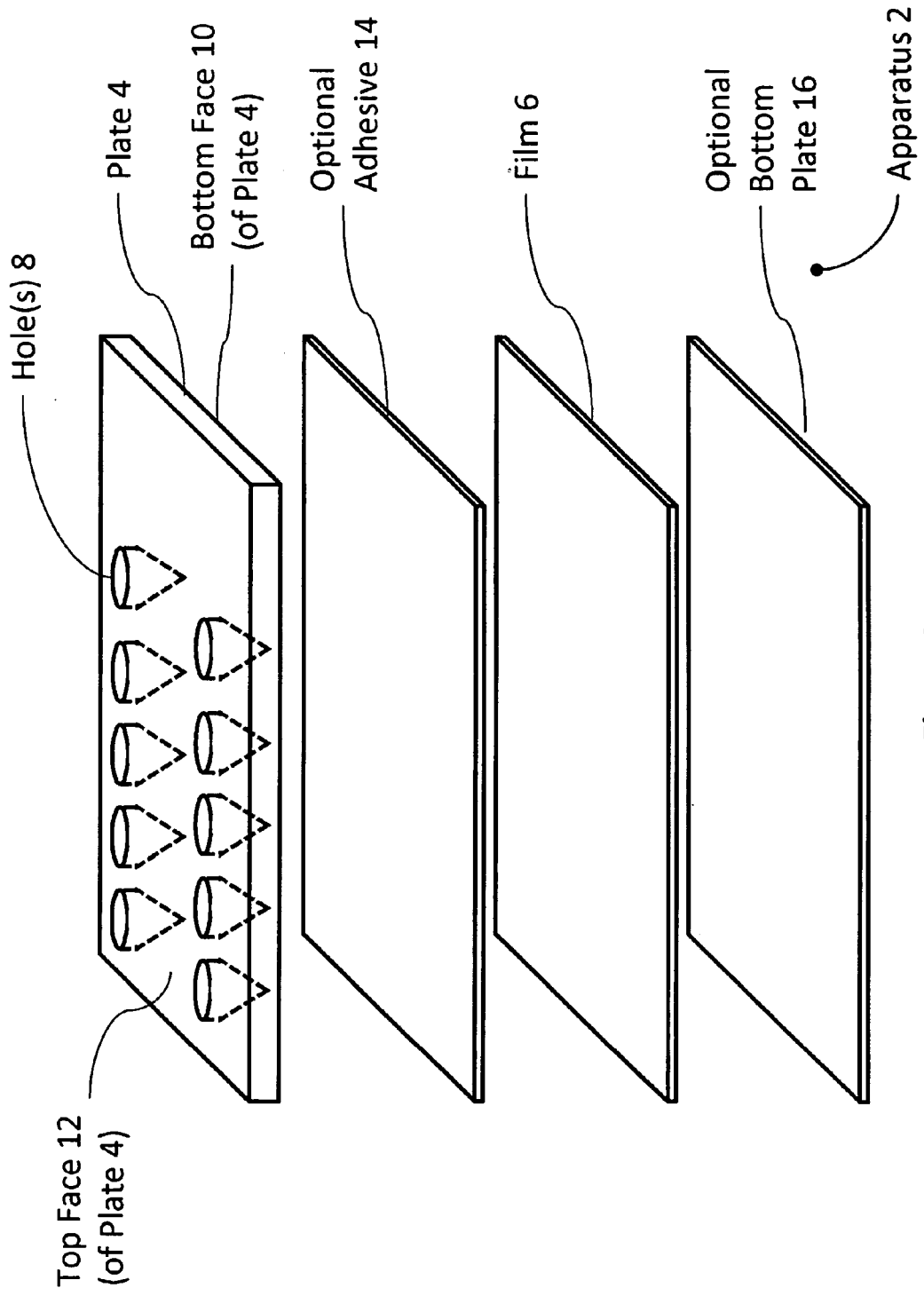
FIG. 1 shows a schematic depiction of the present invention.
Figure 2:
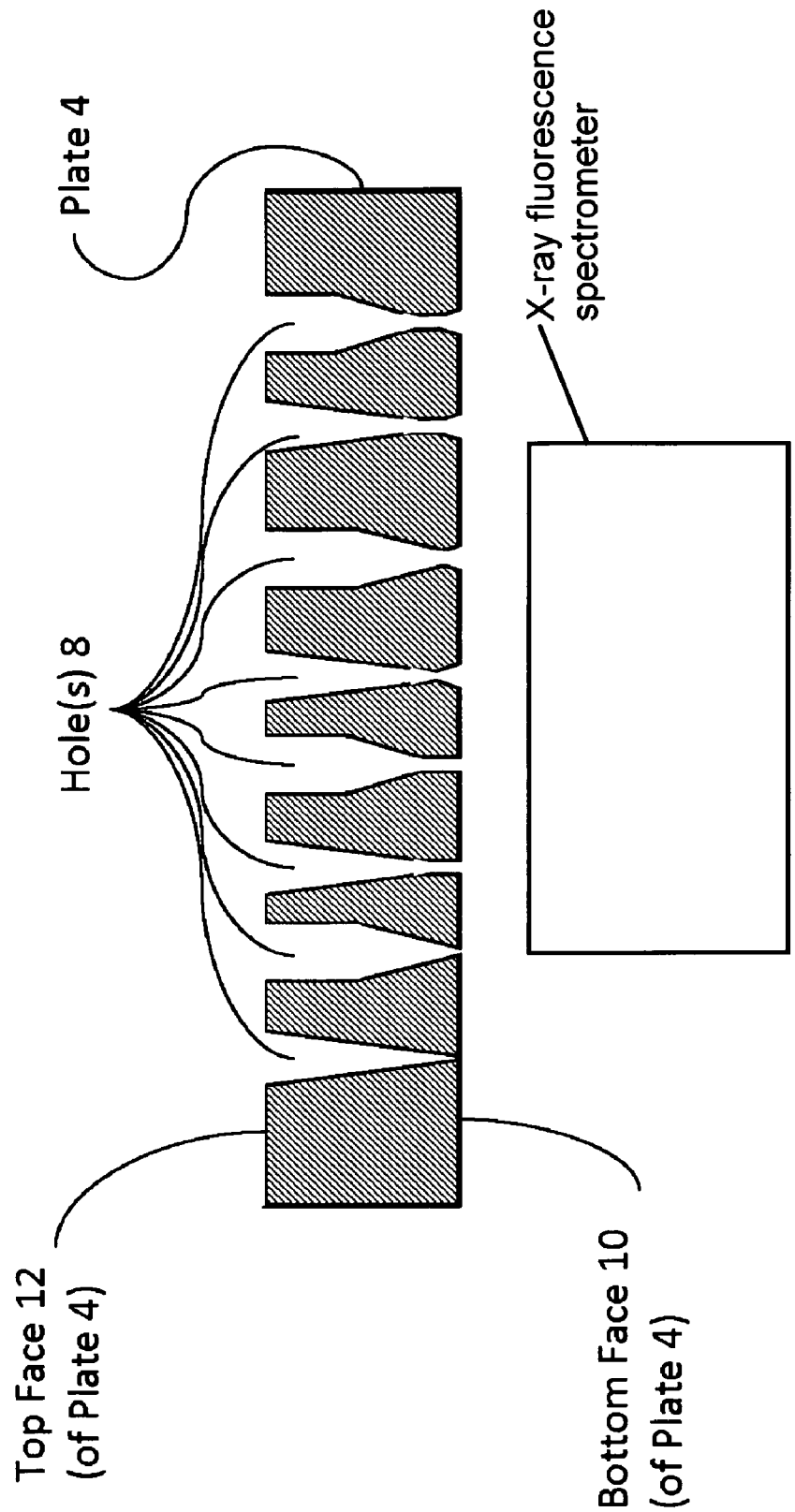
FIG. 2 shows a cutaway view of Plate 4 showing examples of the shapes of Hole(s) 8.

Briefly, the present invention includes an apparatus for preparing samples for measurement by x-ray fluorescence spectrometry. The apparatus comprises a plate having one or more holes passing through the plate. The holes are covered by a film on one side of the plate. The holes are less than 500 micrometers across in one dimension where the film covers the holes. The film is translucent to x-rays. The present invention also includes an apparatus for preparing samples for measurement by x-ray fluorescence spectrometry. The apparatus comprises a plate having one or more holes passing through the plate. The holes are covered on one side of the plate by a detachable cover forming a water-tight seal against the plate. The cover is substantially free of the elements osmium, yttrium, iridium, phosphorus, zirconium, platinum, gold, niobium, mercury, thallium, molybdenum, sulfur, lead, bismuth, technetium, ruthenium, chlorine, rhodium, palladium, argon, silver, and thorium. The holes are less than about 500 micrometers across in one dimension where the cover covers the holes. The present invention also includes a method for preparing samples for measurement by x-ray fluorescence spectrometry. The method comprises providing a solution with less than 10 micromolar solute and a volume of between about 2 microliters and about 2 milliliters. The solution is concentrated and analyzed using x-ray fluorescence spectrometry.

The present invention comprises Apparatus 2, which includes Plate 4 and Film 6. Film 6 covers one face of Plate 4. Plate 4 has one or more Holes 8. Holes 8 pass through Plate 4 from the face of Plate 4 which is covered by Film 6 to the opposite face of Plate 4. Film 6 may be bonded to Plate 4.

Apparatus 2 should not leak solvent at the junction of Film 6 and Plate 4. Preferably, the junction of Film 6 and Plate 4 maintains a water-tight seal when Apparatus 2 is subjected to either temperatures in excess of about 100° F., or acceleration in excess of about 20 times the earth's gravitational constant at sea level, or atmospheric pressure less than about 760 torr.

The dimensions of Plate 4 are more preferably 127.76 mm±0.25 mm by 85.48 mm±0.25 mm, when measured from a position within 12.7 mm (0.5000 inches) of the outside corners of Plate 4. If Plate 4 is substantially rectangular or if Plate 4 has a flange on the bottom, then Plate 4 or its flange preferably has a corner radius to the outside of 3.18 mm±1.6 mm. If Plate 4 is substantially rectangular with has one or more chamfers or beveled corners, then the corner radii of any non-beveled corners are preferably 3.18 mm±1.6 mm to the outside. If Apparatus 2 comprises 96 Hole(s) 8, then Hole(s) 8 are preferably arranged as eight rows by twelve columns. In this case, the distance between at least one outside edge of Plate 4 and the center of the first column of Hole(s) 8 is preferably 14.38 mm±4 mm. The distance between each column of Hole(s) 8 is preferably 9 mm±4 mm. The distance between at least one outside edge of Plate 4 and the center of the first row of Hole(s) 8 is preferably 11.24 mm±4 mm. The distance between each row of Hole(s) 8 is preferably 9 mm±4 mm. At least one of Hole(s) 8 is preferably marked in a distinguishing manner, and more preferably each row is marked in a distinguishing manner and each column is marked in a distinguishing manner. If Apparatus 2 comprises 384 Hole(s) 8, then Hole(s) 8 are preferably arranged as sixteen rows by twenty-four columns. In this case, the distance between at least one outside edge of Plate 4 and the center of the first column of Hole(s) 8 is preferably 12.13 mm±4 mm. The distance between each column of Hole(s) 8 is preferably 4.5 mm±2 mm. The distance between at least one outside edge of Plate 4 and the center of the first row of Hole(s) 8 is preferably 8.99 mm±4 mm. The distance between each row of Hole(s) 8 is preferably 4.5 mm±2 mm. At least one of Hole(s) 8 is preferably marked in a distinguishing manner, and more preferably each row is marked in a distinguishing manner and each column is marked in a distinguishing manner. If Apparatus 2 comprises 1536 Hole(s) 8, then Hole(s) 8 are preferably arranged as thirty-two rows by forty-eight columns. In this case, the distance between at least one outside edge of Plate 4 and the center of the first column of Hole(s) 8 is preferably 11.005 mm±4 mm. The distance between each column of Hole(s) 8 is preferably 2.25 mm±1 mm. The distance between at least one outside edge of Plate 4 and the center of the first row of Hole(s) 8 is preferably 7.865 mm ±4 mm. The distance between each row of Hole(s) 8 is preferably 2.25 mm ±1 mm. At least one of Hole(s) 8 is preferably marked in a distinguishing manner, and more preferably each row is marked in a distinguishing manner and each column is marked in a distinguishing manner. Plate 4 is preferably between 7 mm and 35 mm in height. Top Face 12 and Bottom Face 10 are preferably substantially parallel to each other. Plate 4 may comprise a flange on one or more sides of Plate 4. If Plate 4 comprises a flange, then the height of the flange is preferably between 1 mm and 10 mm, and more preferably is 2.41 mm±0.38 mm or 6.10 mm±0.38 mm or 7.62 mm±0.38 mm when measured from the bottom-resting plane of Plate 4 to the top of the flange. It is preferable that if Plate 4 is substantially rectangular, with or without chamfers on any corners, that the flanges on at least two of the sides of Plate 4 have the same flange height when measured from the bottom-resting plane of Plate 4 to the top of the flange. The flange preferably extends from Plate 4 by at least 0.5 mm and preferably by 1.27 mm when measured at the top of the flange. Any chamfers preferably do not have flanges. A flange on Plate 4 may have interruptions or projections. Preferably, any edge of any interruption or projection on a flange is a minimum of 47.8 mm from the edges of Plate 4 which are substantially perpendicular to the flange having the interruption(s) or projection(s).

Plate 4 is preferably composed of plastic, although the use of metal to compose Plate 4 will make Plate 4 more durable. Plate 4 preferably has dimensions of a length of 5.0299 inches (plus or minus 0.5 inches) by a width of 3.3654 inches (plus or minus 0.5 inches). The height of Plate 4 is preferably between 1 millimeter and 150 millimeters. Plate 4 most preferably conforms to ANSI/SBS 1-2004 and ANSI/SBS 2-2004. Plate 4 has a Top Face 12 and a Bottom Face 10.

Plate 4 has one or more Holes 8, which pass through Bottom Face 10 of Plate 4 and Top Face 12 of Plate 4. If there are ninety-six (96) Holes 8, or three hundred and eighty-four (384) Holes 8, or one thousand five hundred and thirty-six (1,536) Holes 8, then the positioning of the Holes 8 preferably conforms to ANSI/SBS 4-2004. Holes 8 pass through Plate 4. On the Top Face 12, Hole 8 has a diameter of between 500 micrometers and thirty (30) millimeters. On the Bottom Face 10, Hole(s) 8 have a diameter of between 10 micrometers and two millimeters, and preferably a diameter of between 50 micrometers and 500 micrometers, and most preferably a diameter of between 50 micrometers and 350 micrometers. Each Hole 8 preferably has a volume sufficient to hold at least 10 microliters between the planes defined by Top Face 12 and Bottom Face 10. Each Hole 8 may optionally be coated with silicone or another coating that minimizes protein binding to the walls of Hole 8. Hole(s) 8 may be conical or truncated conical with the wide end of the cone at the Top Face 12 of Plate 4 and the narrow end of the cone at the Bottom Face 10 of Plate 4. Hole(s) 8 may be cylindrical at the top and conical or truncated conical at the bottom. Hole(s) 8 may be cylindrical at the top and conical or truncated conical in the middle, and cylindrical at the bottom. Hole(s) 8 may be cylindrical at the top and conical or truncated conical in the middle, and conical at the bottom with wide end of the bottom cone opening onto Bottom Face 10 of Plate 4; in this configuration, Hole(s) 8 are dumbbell shaped. Any shape which allows liquid to flow through Hole(s) 8 is acceptable. The perimeter at the widest part of Hole(s) 8 is preferably greater than the perimeter of Hole(s) 8 where Hole(s) 8 is covered by Film 6.

Hole(s) 8 should be chemically inert under the conditions of use. Preferably, Hole(s) 8 do not release contaminants that interfere with the XRF measurements of Sample 18. More preferably, Holes(8) do not release more than 5 parts per billion sulfur or 5 parts per billion chlorine or five parts per billion phosphorus in any chemical form when exposed to a solution comprising water, proteins, dimethylsulfoxide or dimethylformamide at 50° C. for 3 hours.

Hole(s) 8 are also preferably smooth so that Sample 18 does not become entrained in rough surfaces. Any surface features in Hole(s) 8 preferably are less than 200 microns in the dimension normal to the inside face of Hole(s) 8. The inside face of Hole(s) 8 preferably has a root mean squared (RMS) roughness of less than about 20 micrometers. A Hole (8) having an internal depression of 200 micrometers functioned acceptably in the present invention. Hole (8) having a roughness of approximately 5 micrometers functioned acceptably in the present invention. To minimize the amount of Sample 18 that becomes adhered to the side of Hole(s) 8, Hole(s) 8 should have an included angle of less than about 45 degrees, and more preferably less than about 42 degrees, and most preferably less than about 40 degrees. The entire Hole(s) 8 can have these included angles, or just the portion of Hole(s) 8 where the cross sectional area is being reduced can be shaped to have this included angle.

The line defining the interface between the solution, the solid surface of Hole(s) 8, and the atmosphere is called the contact line. Hole(s) 8 are preferably shaped so that the length of the contact line diminishes for at least a portion of the time in which the volume of the solution is reduced. It is desirable that a portion of Sample 18 adhere to Film 6 if Film 6 is detached; therefore, it is desirable that Hole(s) 8 be wider where it adjoins Film 6 than where Hole(s) 8 is at its narrowest.

The Hole(s) 8 should have a small cross sectional area at the bottom, i.e. the location where the Hole(s) 8 adjoins Film 6. The cross section of Hole(s) 8 at this location are preferably less than about 500 micrometers across in one dimension, and are more preferably less than 1000 micrometers across in the other dimension, so that the entire cross sectional area of Hole(s) 8 at the location where Hole(s) 8 adjoin Film 6 is less than about 0.005 square centimeters.

Film 6 is located across the Bottom Face 10 of Plate 4. Film 6 may be held against Bottom Face 10 of Plate 4 by an optional Adhesive 14. Alternatively, Film 6 may be held against Bottom Face 10 of Plate 4 by an optional Bottom Plate 16, in which case Film 6 is placed between Bottom Plate 14 and Bottom Face 10 of Plate 4. A Gasket 20 may be placed between Film 6 and Bottom Plate 16. Film 6 may be bonded to Bottom Face 10 of Plate 4 by heat or by a solvent. Film 6 may be permanently attached to Plate 4 or it may be removable. Film 6 is preferably substantially free of the at least one of the elements sulfur, phosphorus, or chlorine. Examples of suitable materials include Porvair #229302, Porvair #229112, Porvair #229058, Porvair #229304, and Porvair #229301, all of which are available from Porvair plc, Brampton House, 50 Bergen Way, King's Lynn, Norfolk PE30 2JG, U.K.), aluminum foils (examples: Microseal 'F' Foil from Bio-Rad Laboratories, 1000 Alfred Nobel Drive, Hercules, Calif. 94547). Other tapes that may be used for Film 6 include: Super-Thin Polyester Surface-Protection Tape, Chemical-Resistant Surlyn Surface-Protection Tape, Abrasion-Resistant Polyurethane Surface-Protection Tape, Heat-Resistant Kapton Tape with Silicone Adhesive or with Acrylic Adhesive, UV-Resistant Polyethylene Surface-Protection Tape, Clean-Release Polyethylene Surface-Protection Tape, Low-Static Polyimide Tape, all available from McMaster-Carr, 6100 Fulton Industrial Blvd., Atlanta, Ga. 30336-2852. Other materials which may be used for Film 6 include 0.02 micrometer thick, 99.99% pure gold foil, available from Lebow Company, 5960 Mandarin Ave., Goleta, Calif. 93117 U.S.A.; 0.07 micrometer thick, 99.95% pure aluminum foil, available from Lebow Company, 5960 Mandarin Ave., Goleta, Calif. 93117 U.S.A.; 0.1 micrometer through 20 micrometer thick PARYLENE N®, available from Lebow Company, 5960 Mandarin Ave., Goleta, Calif. 93117 U.S.A.; and 0.5 micrometer thick to 25.0 micrometer thick, 99.99% pure titanium foil, available from Lebow Company, 5960 Mandarin Ave., Goleta, Calif. 93117 U.S.A.; and 4 micrometer thick to 8 micrometer thick polypropylene, available from Lebow Company, 5960 Mandarin Ave., Goleta, Calif. 93117 U.S.A. Other substrates that are conveniently used are AP1, AP3, ProLINE Series 10, ProLINE Series 20, DuraBeryllium substrates from Moxtek, 452 West 1260 North, Orem, Utah 84057. Other materials which may be used for Film 6 are Ultralene®, mylar, polycarbonate, prolene, and kapton, available from SPEX CertiPrep Ltd, 2 Dalston Gardens, Stanmore, Middlesex HA7 1BQ, ENGLAND. Other materials that may be conveniently used are Hostaphan®, polyester, and Etnom®, available from Chemplex Industries, Inc., 2820 SW 42nd Avenue, Palm City, Fla. 34990-5573 USA. Another material that may be conveniently used is Zone Free Film Part ZAF-PE-50, available from Excel Scientific, 18350 George Blvd, Victorville, Calif., 92394. This list is not exhaustive, and other materials may be used for Film 6. Film 6 may be made of fluorocarbons. Film 6 is also preferably substantially free of elements which have X-Ray Fluorescence emission peaks having energies of between 1.9 KeV and 3 KeV, because these peaks tend to interfere with the signals of most interest for the application of Apparatus 2 to biochemical and biological applications. Elements which have X-Ray Fluorescence emission peaks having energies of between 1.9 KeV and 3 KeV are: osmium, yttrium, iridium, phosphorus, zirconium, platinum, gold, niobium, mercury, thallium, molybdenum, sulfur, lead, bismuth, technetium, ruthenium, chlorine, rhodium, palladium, argon, silver, and thorium. If Apparatus 2 is used with an x-ray fluorescence spectrometer which uses an x-ray detector which comprises silicon, then Film 6 is also preferably free of elements which have X-Ray Fluorescence escape peaks (i.e. x-ray fluorescence emission peaks minus 1.74 KeV) having energies of between 1.9 KeV and 3 KeV, because these escape peaks tend to interfere with the signals of most interest for the application of Apparatus 2 to biochemical and biological applications. Elements which have X-Ray Fluorescence escape peaks having energies of between 1.9 KeV and 3 KeV are: calcium, tellurium, iodine, scandium, xenon, cesium, barium, titanium, and lanthanum. "Substantially free" is defined herein as being less than about 4% by weight. Film 6 may have additional chemical elements, which may be used for measuring the thickness of Sample 18. If wavelength dispersive x-ray fluorescence is used, then the elemental purity of Film 6 is not as important; in this case, the film should be substantially free of the element or elements which are being used to quantify the sample. Film 6 may be treated to increase protein adhesion; a non-inclusive list of treatments includes treating Film 6 with oxygen or nitrogen plasma or with poly-lysine.

If Film 6 is bonded to Plate 4, then the Film 6 should deform with Sample 18. Film 6 deforms from the plane defined by the perimeter of Hole(s) 8 where Hole(s) 8 adjoins Film 6, by a minimum distance of 100 nanometers.

If Film 6 is detachable from Plate 4, then the Plate 4 deforms as a result of loading during normal use. Plate 4 is deformed from the plane Film 6 by a minimum distance of 10 micrometers.

If Film 6 is not detachable from Bottom Face 10 of Plate 4, then Film 6 is preferably translucent to x-rays having energies of 2.3 KeV. In this case, translucent is defined as allowing at least 5% of the x-rays which are normal to Film 6 and which have an energy of 2.3 KeV to pass through Film 6, when Film 6 is placed in a plane which is perpendicular to a line defined by Sample 18 and an x-ray detector. The material compositions and thicknesses which may be used for Film 6 (if Film 6 is not detachable from Bottom Face 10 of Plate 4) may be measured or calculated using x-ray attenuation parameters for various materials. A non-exhaustive list of materials which are suitable for Film 6 (if Film 6 is not detachable from Bottom Face 10 of Plate 4) includes polypropylene which is less than about 195 micrometers thick, and polycarbonate which is less than about 105 micrometers thick.

Apparatus 2 is used with an x-ray fluorescence spectrometer. Apparatus 2 is preferably used by placing a solution of Sample 18 in one or more Hole(s) 8. At least a portion of the solvent containing Sample 18 is then evaporated. Preferably at least 80% of the solvent of Sample 18 is evaporated; more preferably, substantially all of the solvent of Sample 18 is evaporated. The solvent is preferably evaporated using elevated temperatures that are above about 22° C. or reduced atmospheric pressure that is below about 760 torr. Apparatus 2 is preferably placed in a vacuum centrifuge, such as a Savant Speed Vac Plus SC 250DDA or a Thermo Savant SPD 1010 SpeedVac®. Solvent is preferably removed from Sample 18 while Apparatus 2 is centrifuged, and the Sample 18 is concentrated by being collected at the portion of Hole 8 which passes through Bottom Face 10 of Plate 4 and onto Film 6. The advantage of the Apparatus 2 is that the sample is concentrated into a small area. If Film 6 is detachable and Film 6 is thick enough that it is not translucent (translucent is defined as allowing at least 5% of the x-rays which are normal to Film 6 and which have an energy of 2,300 eV to pass through Film 6, when Film 6 is placed in a plane which is perpendicular to a line defined by Sample 18 and an x-ray detector), then Film 6 is then detached from Plate 4 and measured in an X-ray Fluorescence Spectrometer (for example, an EDAX Eagle III µprobe, available from EDAX, 91 McKee Drive Mahwah, N.J. 07430; or a MicroXR VXR Microbeam XRF System, available from Thermo Fisher Scientific, Inc., 81 Wyman Street, Waltham, Mass. 02454). In this case, Film 6 is oriented in the X-ray fluorescence spectrometer so that Sample 18 is between Film 6 and the x-ray detector of the x-ray fluorescence spectrometer. Film 6 is preferably held in a Frame 20 to hold Film 6 flat. If Film 6 is translucent to x-rays as defined above, then Sample 18 may be measured without detaching Film 6 from Plate 4. If Film 6 is translucent to x-rays, then Sample 18 may be measured using an x-ray fluorescence spectrometer with Film 6 oriented between Sample 18 and the x-ray detector, whether or not Film 6 is detached from Plate 4. The advantage of not detaching Film 6 from Plate 4 is that Plate 4 functions as a frame, and therefore no additional Frame 20 is necessary. The advantage of detaching Film 6 is that Sample 18 may be measured with no attenuation from Film 6. Apparatus 2 is preferably used with an x-ray fluorescence spectrometer whose beam size is matched to the size of Sample 18 after the solvent has been evaporated; in this case a matched beam size is defined as the area of the x-ray excitation beam which contains at least 80% of the x-ray flux which is incident on Sample 18 is within a factor of 100 of the area of Sample 18. The x-ray excitation source may be focused, such as a by means of a polycapillary focusing optics offered by X-Ray Optical Systems, Inc., 15 Tech Valley Drive, East Greenbush, N.Y. 12061. An x-ray fluorescence spectrometer equipped with a collimator or another type of focusing optic on the x-ray excitation source is also acceptable.

The advantage of using Apparatus 2 for preparing samples for x-ray fluorescence spectrometry measurements is that the measurement limits are better when using Apparatus 2 versus simply pipetting or printing a sample on a film as described in Miller T C et al. "Semiconductor applications of manlier droplet methodology with total reflection x-ray fluorescence analysis." Spectrochimica Acta B. 2004, 59:1117-1124; or Miller T C and G J Avilla. "Nanodroplets: a new method for dried spot preparation and analysis" X-Ray Spect 2004, 33:101-106, for example. The second advantage of using Apparatus 2 is that many biological samples are prepared as dilute solutions, for example as dilute solutions of proteins. Apparatus 2 allows relatively large volumes of a solution of sample to be prepared, and the sample to be concentrated into a dried spot of sample with optimum properties. Volumes of solution are preferably between 2 microliters to 2 milliliters, and more preferably are between 10 microliters and 250 microliters. In contrast, existing sample preparation methods require highly concentrated sample solutions in order to deposit a sufficient amount of sample for measurement. Also in contrast, existing sample preparation methods require a large amount of sample to prime their printer head or fill their reservoirs, which wastes valuable sample. For example, assume one desires to measure approximately 30 picograms of sulfur in a sample. Using standard deposition methods, which might use 10 nanoliters of solution, the concentration of sulfur in the initial solution would have to be 100 micromolar. Using Apparatus 2, 100 microliters of solvent may be used, resulting in an initial sample concentration of 10 anomala. For biology, biochemistry, and drug development, it is important to be able to work with solutions which have anomala concentration, versus solutions with tens or hundreds of micromolar concentrations. If Apparatus 2 is used with a protein or a nucleic acid, the mass of the sulfur or phosphorus or a combination of sulfur and phosphorus in the protein or nucleic acid is preferably between 50 femtograms and 1 microgram, and most preferably the mass of the phosphorus or sulfur or combinations thereof in Sample 18 is between 100 picograms and 100 nanograms.

Sample 18 is deposited in a shape which is defined by the shape of Hole 8 as it penetrates the Bottom Face 10 of Plate 4. The most efficient shape for Sample 18 is one which is similar to the size of the x-ray excitation beam of the x-ray fluorescence spectrometer. Usually, both Sample 18 and the x-ray excitation beam are roughly circular in outline. Similarity, in this context, means that the area of Sample 18 is within a factor of 100 times greater or smaller than the area of the x-ray excitation beam as it illuminates Sample 18 (for example, the diameter of Sample 18 is within a factor of 10 of the x-ray excitation beam as it illuminates Sample 18). Preferably, Sample 18 is within a factor of 25 times bigger or smaller than the area of the x-ray excitation beam as it illuminates Sample 18 (for example, the diameter of Sample 18 is within a factor of 5 of the x-ray excitation beam as it illuminates Sample 18). If the area of x-ray excitation beam as it illuminates Sample 18 is significantly greater than the area of Sample 18, then x-ray photons are wasted. If the area of x-ray excitation beam as it illuminates Sample 18 significantly smaller than the area of Sample 18, then the measurement time will be unnecessarily long or else a portion of Sample 18 will be wasted by its not being measured.

Sample 18 typically comprises an aqueous sample of a protein or nucleic acid, which has been optionally modified by addition of an inhibitor, co-factor, metal, protein, sugar, or other chemical. Sample 18 may be conveniently measured using an X-ray fluorescence instrument. This x-ray fluorescence instrument preferably comprises at least one of the following: a monocapillary focusing optic, polycapillary focusing optic, a collimator, a microfocus X-ray tube, a synchrotron X-ray source, a linear accelerator X-ray source, a rhodium X-ray tube, a molybdenum X-ray tube, a chromium X-ray tube, a silver X-ray tube, a palladium X-ray tube, a monochromatic X-ray source, a polychromatic X-ray source, a polarized X-ray source, a confocal X-ray fluorescence spectrometer focusing arrangement, a PIN diode detector, a semiconductor X-ray detector, a germanium or doped germanium X-ray detector, a silicon or doped silicon X-ray detector, a wavelength dispersive X-ray fluorescence spectrometer, an energy dispersive X-ray fluorescence spectrometer, total reflectance X-ray fluorescence spectrometer, and the like.

Figure 3:
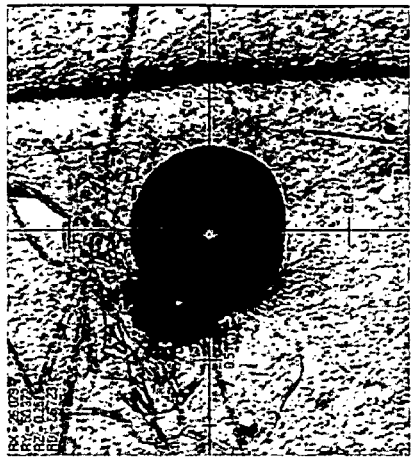
FIG. 3 shows protein samples prepared using Apparatus 2 and by pipette.
Figure 3:
Figure 4:
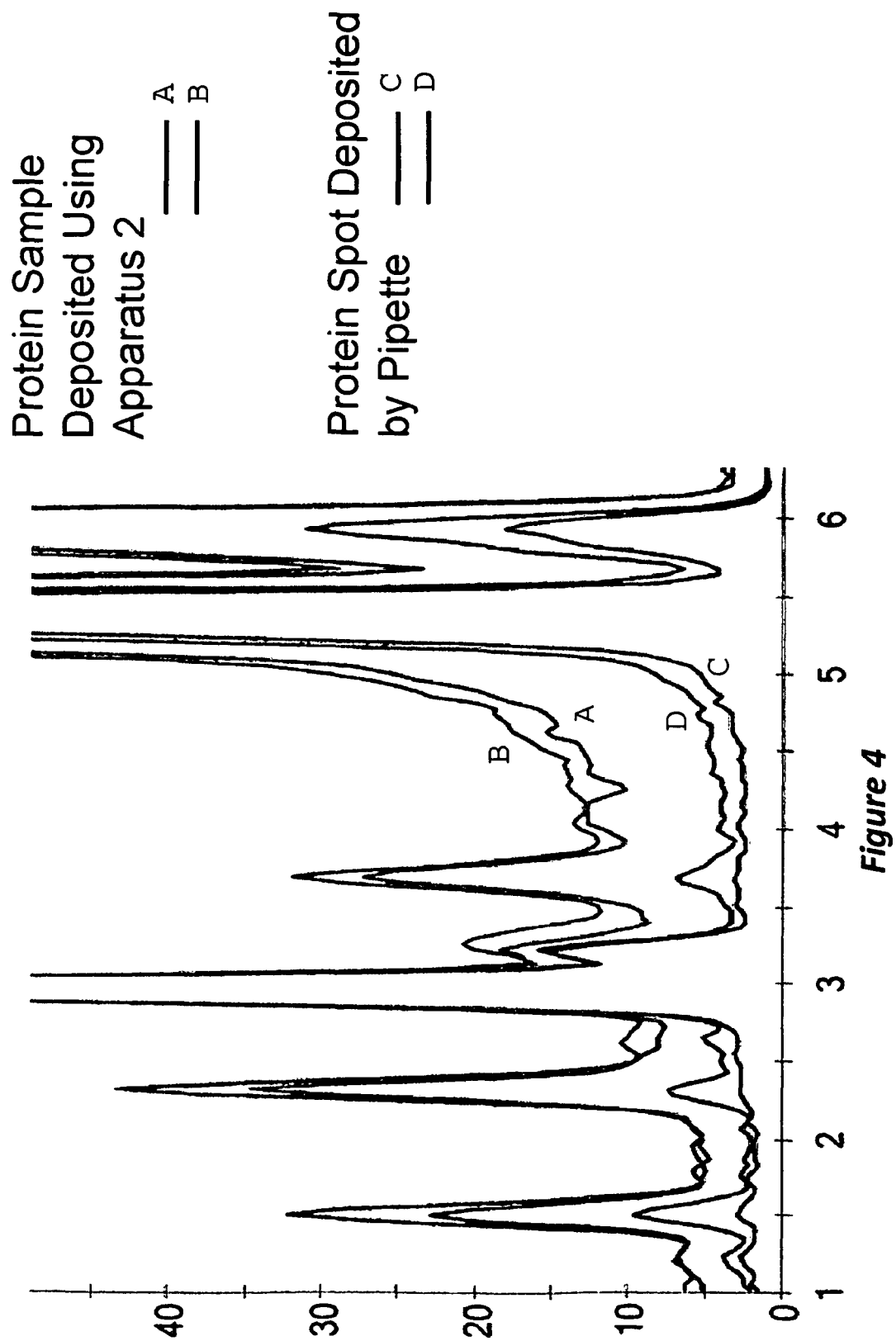
FIG. 4 shows x-ray fluorescence spectra of protein samples prepared using Apparatus 2 and by pipette.
Figure 5:
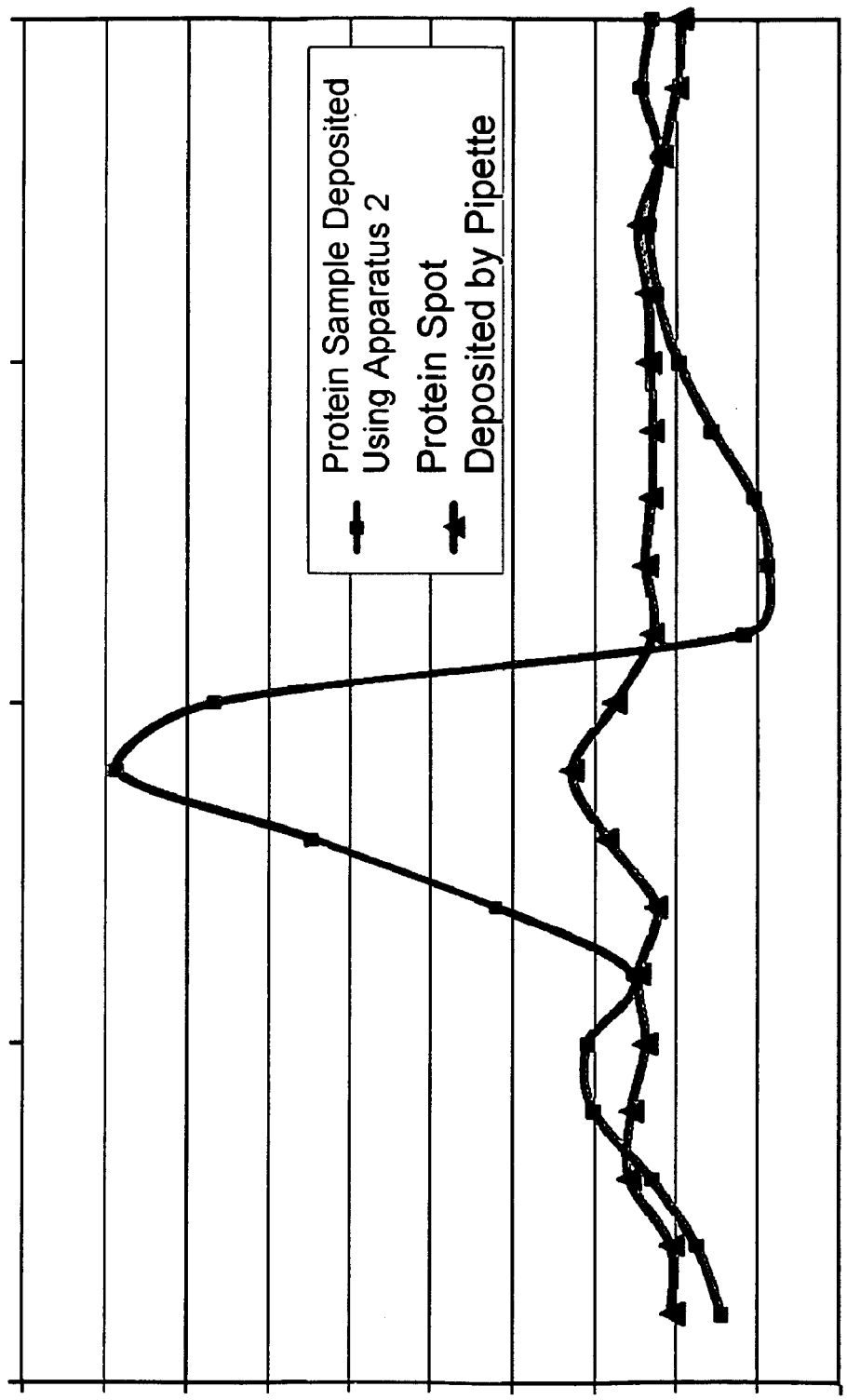
FIG. 5 shows a comparison of the cross-sectional thickness profile of protein samples prepared using Apparatus 2 and by pipette.

If Film 6 contains additional chemical elements which are measurable with the x-ray fluorescence spectrometer being used with Apparatus 2, then these elements may be used to measure the thickness of Sample 18. For example, if Film 6 contains silicon, then the attenuation of the silicon x-ray signal by Sample 18 will allow the thickness of Sample 18 to be estimated. FIG. 5 shows the relative thicknesses of a protein sample deposited using Apparatus 2 and a protein sample deposited using a pipette. The protein sample deposited using Apparatus 2 is significantly more compact and lacks the ring shape as compared with samples deposited by pipette which display alternating rings of deposited sample and rings that are depleted in sample. FIG. 3 shows a photograph of a sample deposited by pipette. FIG. 3 also shows a photograph of a sample deposited using Apparatus 2. The sample deposited using a pipette is significantly larger and has more rings than the sample deposited using Apparatus 2. The more compact sample deposited using Apparatus 2 provides a more intense signal in the x-ray fluorescence spectrum, as shown in FIG. 4. Thickness corrections are performed by measuring the signal from Film 6 (e.g. a silicon signal) in a region where there is no Sample 18, and measuring the same elemental signal from a region of Film 6 which is covered by Sample 18. The difference in the x-ray signal from the film may be related to the thickness of Sample 18 by calculating the thickness of Sample 18 required to attenuate the x-ray signal by the measured amount.

Apparatus 2 may be used with proteins. Many proteins require a buffer to maintain the pH within a particular range (e.g. a pH buffer), or to maintain the redox state of a chemical (e.g. a redox buffer), or to maintain an ionic strength (e.g. an isotonic buffer). Many buffers contain elements which might interfere with the measurement of the chemical. The buffer should preferably be free of at least one chemical element having an atomic number of greater than four, where that chemical element is present in Sample 18. The buffer should more preferably be free of at least one chemical element having an atomic number of greater than eight, where that chemical element is present in the Sample 18. The buffer should preferably be free of at least one of the following chemicals or functional groups: dimethylsulfoxide, thiols, sulfate anion, sulfonate anions, chloride anion, bromide anion, fluoride anion, iodide anion, perchlorate anion, phosphate anion, and phosphonate anions. The buffer preferably comprises one or more of the following chemical or functional groups: amine, imine, nitrate anion, nitrite anion, ammonium cation, acetate anion, carboxylate anion, carbonate anion, and iminium cation; these chemicals offer the correct buffering properties with minimal x-ray fluorescence interference. Most preferably, the buffer comprises an ammonium nitrate salt such as tris(ethanol)amine nitrate, also known as tris nitrate.

The proteins to be used with the present invention are preferably purified to remove chemicals, including pH buffers and redox buffers and isotonic buffers, that are not chemically bound or which are loosely bound to the protein. This purification also removes salts that contribute to poor sample quality. Loosely bound is defined as meaning having a binding affinity that is weaker than about ten millimolar. This desalting step may be conducted conveniently using gel filtration chromatography or size exclusion chromatography, such a Quick Spin Protein Column using Sephadex G-25, available from Roche Applied Science, PO Box 50414, Indianapolis, Ind., 46250. This process is amenable to multiplexing using a well plate format, such as a 96-well, 384-well, or 1536-well plate format. Separations systems such as Zeba 96-well plates available from Pierce Biotechnology Inc., PO Box 117, Rockford, Ill., 61105, are particularly convenient. The advantage of removing the buffers and other loosely bound chemicals is that their removal minimizes interfering elements which might attenuate the desired X-ray fluorescence signal or add spurious x-ray fluorescence signals, or which create non-fluorescent x-ray signals through diffraction and other similar processes.

Both single-plexed or multiplexed gel filtration chromatography process may be expedited using a centrifuge, such as a the IEC CL40 available from Thermo Fisher Scientific, product #11210923, 450 Fortune Blvd, Milford, Mass., 01757; or a vacuum manifold, such as a Vacuum apparatus such as the MultiScreen Vacuum manifold with Direct Stack from Millipore, 290 Concord Road, Billerica, Mass. 01821, attached to a standard vacuum pump (for example, Millipore, Catalog # WP61 115 60) also available from Millipore. Separations are preferably carried out in less than 300 seconds of centrifugation, and are more preferably carried out in less than 30 seconds of centrifugation. An alternative method of separation is ultrafiltration, such as might be performed using a Centricon YM-3 centrifuged for 3 hours at 7000 g.

Desalting by size exclusion columns may be conveniently used with Apparatus 2, by using a desalting well plate having the same number of wells and locations of wells as the number and location(s) of Hole(s) 8 in Apparatus 2. The desalting plate is placed on top of Apparatus 2, and a solution of Sample 2 is placed in one or more of the wells of the desalting plate. The stacked desalting plate and Apparatus 2 are centrifuged until solution containing Sample 18 passes through the desalting plate and into Hole(s) 8 of Apparatus 2. Apparatus 2 is then placed in a vacuum centrifuge as described above. Alternatively, the solution of Sample 18 may be desalted and transferred to Apparatus 2, for example by pipette.

If Sample 18 comprises a protein, it should preferably be present at a concentration of less than 10 micromolar and more preferably less than 100 nanomolar. In addition to proteins, other biological molecules which may be used include nucleic acids, polysaccharides, peptides, and other biologically derived molecules; like proteins, these are preferably present in solution at concentrations less than 10 micromolar and more preferably less than 100 nanomolar.

The foregoing description of the invention has been presented for purposes of illustration and description and is not intended to be exhaustive or to limit the invention to the precise form disclosed, and obviously many modifications and variations are possible in light of the above teaching.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for preparing a sample for measurement by x-ray fluorescence spectrometry, comprising providing a solution having a concentration of solute less than 10 micromolar and a volume of between 2 microliters and 2 milliliters, concentrating the solution into a sample having less than one-fifth of the original volume of the solution, and analyzing the sample using x-ray fluorescence spectrometry.

2. The method of claim 1, wherein the solution comprises a biological molecule having a concentration of less than about 10 micromolar.

3. The method of claim 2, wherein the biological molecule in the solution has a total mass of between 50 femtograms and 1 microgram of an element selected from the list of phosphorus, sulfur, and combinations thereof.

4. The method of claim 1, wherein the sample is dried in a well plate having a well which is less than about 500 micrometers in at least one dimension at the bottom of the well.

5. The method of claim 4, wherein the well has an included angle of less than about 45 degrees.

6. The method of claim 5, wherein the area of the bottom of the well is less than about 0.005 square centimeters.

7. The method of claim 6, wherein the walls of the hole have an RMS roughness of less than about 20 micrometers.

8. The method of claim 7, wherein the well plate has a detachable bottom piece, and at least a portion of the sample remains on the detachable bottom piece when the detachable bottom piece is detached.

9. A method for preparing a sample for measurement by x-ray fluorescence spectrometry, comprising providing a solution having a concentration of solute less than 10 micromolar and a volume of between 2 microliters and 2 milliliters, and concentrating the solution into a sample having less than one-fifth of the original volume of the solution, wherein the solution comprises a biological molecule having a concentration of less than about 10 micromolar.

10. The method of claim 9, wherein the biological molecule in the solution has a total mass of between 50 femtograms and 1 microgram of an element selected from the list of phosphorus, sulfur, and combinations thereof.

11. The method of claim 9, wherein the sample is dried in a well plate having a well which is less than about 500 micrometers in at least one dimension at the bottom of the well.

12. The method of claim 11, wherein the well has an included angle of less than about 45 degrees.

13. The method of claim 12, wherein the area of the bottom of the well is less than about 0.005 square centimeters.

14. The method of claim 13, wherein the walls of the hole have an RMS roughness of less than about 20 micrometers.

15. The method of claim 14, wherein the well plate has a detachable bottom piece, and at least a portion of the sample remains on the detachable bottom piece when the detachable bottom piece is detached.

* * * * *